United States Patent [19]

Kumar et al.

[11] Patent Number: 5,573,712
[45] Date of Patent: *Nov. 12, 1996

[54] SUBSTITUTED NAPHTHOPYRANS

[75] Inventors: Anil Kumar, Pittsburgh; Barry V. Gemert, Murrysville; David B. Knowles, Apollo, all of Pa.

[73] Assignee: Transitions Optical, Inc., Pinellas Park, Fla.

[ * ] Notice: The term of this patent shall not extend beyond the expiration date of Pat. No. 5,458,814.

[21] Appl. No.: 407,830

[22] Filed: Mar. 21, 1995

Related U.S. Application Data

[62] Division of Ser. No. 164,187, Dec. 9, 1993, Pat. No. 5,658,814.

[51] Int. Cl.$^6$ .............. G02B 5/23; G02B 27/00; C07D 311/92
[52] U.S. Cl. .............. 252/586; 549/389; 549/362; 549/331; 549/60; 549/58; 548/454; 546/256; 546/280.4; 546/281.1; 546/282.7; 546/277.4; 546/282.4; 524/110
[58] Field of Search .................. 549/389, 362, 549/331, 60, 58; 548/454; 546/269, 167; 524/110; 252/586

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,816,584 | 3/1989 | Kwak et al. | 544/71 |
| 4,818,096 | 4/1988 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/160 |
| 4,980,089 | 12/1980 | Heller | 252/586 |
| 4,994,208 | 2/1991 | McBain et al. | 252/586 |
| 5,066,818 | 11/1991 | Van Gemert | 549/389 |
| 5,200,116 | 4/1993 | Heller | 252/586 |
| 5,238,981 | 8/1993 | Knowles | 524/110 |
| 5,244,602 | 9/1993 | Van Gemert | 252/589 |

OTHER PUBLICATIONS

*Friedel–Crafts and Related Reactions*, George A. Olah, Interscience Publishers, vol. 3. Chap. XXXI, pp. 1–8, 1964.
"Regioselective Friedel Crafts Acylation of 1,2,3,4–Tetrahydroquinoline and Related Nitrogen Heterocycles: Effects of NH Protective Groups and Ring Size", Ishihara, Y., et al, J. Chem. Soc., Perkin Trans. 1, pp. 3401–3406, 1992.
"Synthesis, Conformation, and Complexation Behavior of 2,9,18,25–Tetraoxa[8,8] (1,4)naphthalenophane", Adams, S. P. et al, J. Org. Chem., vol. 46, pp. 3474–3478, 1981.
*Organic Reactions*, vol. VI, John Wiley and Sons, Inc. Chapter 1, pp. 1–2 (1951).
*Organic Synthesis*, vol. 31, John Wiley and Sons, Inc., pp. 90 and 93 (1951).
*Organic Synthesis*, vol. 32, John Wiley and Sons, Inc., pp. 72 and 77 (1952).

*Primary Examiner*—Nicky Chan
*Attorney, Agent, or Firm*—Frank P. Mallak; Irwin M. Stein

[57] ABSTRACT

Described are novel reversible photochromic naphthopyran compounds, examples of which are compounds having certain substituents at the number 5 and 6 carbon atoms of the naphtho portion of the naphthopyran and at the 2-position of the pyran ring. Certain substituents may also be present at the number 7, 8, 9 or 10 carbon atoms of the naphtho portion of the naphthopyran. Also described are organic host materials that contain or that are coated with such compounds. Articles such as ophthalmic lenses or other plastic transparencies that incorporate the novel naphthopyran compounds or combinations thereof with complementary photochromic compounds, e.g., spiro(indoline) type compounds, are also described.

26 Claims, No Drawings

SUBSTITUTED NAPHTHOPYRANS

This is a division of application Ser. No. 08/164,187, filed Dec. 9, 1993, U.S. Pat. No. 5,658,814.

The present invention relates to certain novel naphthopyran compounds. More particularly, this invention relates to novel photochromic naphthopyran compounds and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to unacceptably long periods of time to fade after activation.

U.S. Pat. No. 3,627,690 describes photochromic 2,2-disubstituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion. U.S. Pat. No. 4,818,096 discloses a blue coloring photochromic benzo- or naphthopyran having at the position alpha to the oxygen of the pyran ring a phenyl group having a nitrogen containing substituent in the ortho or para positions.

The present invention relates to novel substituted 2H-naphtho-(1,2-b)pyran compounds which have been unexpectedly found to have an acceptable fade rate in addition to a high activated intensity and a high coloration rate. In particular, the use of certain substituents at specific locations on the naphtho portion of the naphthopyran compound increases the fade rate without the addition of acids or bases. In addition, these compounds have certain substituents at the number 5 and 6 carbon atoms of the naphtho portion of the naphthopyran, and at the 2-position of the pyran ring. Certain substituents may also be present at the number 7, 8, 9 or 10 carbon atoms of the naphtho portion of the naphthopyran.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

Photochromic compounds that are most useful in optical applications, such as conventional ophthalmic lenses, are those which possess (a) a high quantum efficiency for coloring in the near ultraviolet, (b) a low quantum yield for bleaching with white light, and (c) a relatively fast thermal fade at ambient temperature but not so rapid a thermal fade rate that the combination of white light bleaching and thermal fade prevent coloring by the ultraviolet component of strong sunlight. In addition, the aforesaid properties are desirably retained in conventional rigid synthetic plastic materials customarily used for ophthalmic and plano lenses when such materials have applied to or incorporated therein such photochromic compounds.

In accordance with the present invention, it has now been discovered that certain novel 2H-naphtho[1,2-b]pyran compounds having an acceptable fade rate, high activated intensity and a high coloration rate may be prepared. These compounds may be described as naphthopyrans having certain substituents at the 2 position of the pyran ring and at the number 5 and 6 carbon atoms of the naphtho- portion of the naphthopyran ring. Certain substituents may also be present at the 7, 8, 9 or 10 carbon atoms of the naphtho portion of the naphthopyran ring. These compounds may be represented by the following graphic formula:

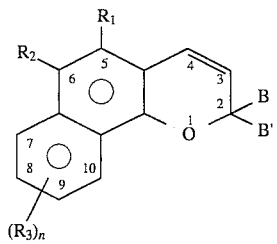

In graphic formula I, $R_1$ is the group, —C(O)W, W being —$OR_4$ or —$N(R_5)R_6$, wherein $R_4$ is hydrogen, allyl, $C_1$–$C_6$ alkyl, e.g., methyl, ethyl, propyl, butyl, pentyl, and hexyl, phenyl, mono($C_1$–$C_6$)alkyl substituted phenyl, mono($C_1$–$C_6$)alkoxy-substituted phenyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, ($C_1$–$C_6$)alkoxy($C_2$–$C_4$)alkyl, or $C_1$–$C_6$ haloalkyl; and $R_5$ and $R_6$ may each be selected from the group consisting of hydrogen, $C_1$–$C_6$ alkyl, $C_5$–$C_7$ cycloalkyl, phenyl and mono- or di-substituted phenyl. The phenyl substituents may be $C_1$–$C_6$ alkyl and $C_1$–$C_6$ alkoxy and the halo substituents may be chloro or fluoro.

More preferably, $R_1$ is the group, —C(O)W, W being the groups —$OR_4$ or —$N(R_5)R_6$, wherein $R_4$ is hydrogen, $C_1$–$C_4$ alkyl, phenyl, mono($C_1$–$C_4$)alkyl substituted phenyl, mono($C_1$–$C_4$)alkoxy substituted phenyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl($C_1$–$C_2$)alkyl, mono($C_1$–$C_4$)alkoxy($C_2$–$C_3$)alkyl, or $C_1$–$C_4$ haloalkyl; and $R_5$ and $R_6$ may each be selected from the group consisting of hydrogen, $C_1$–$C_4$ alkyl, $C_5$–$C_7$ cycloalkyl, phenyl and mono- or di-substituted phenyl. The phenyl substituents may be selected from $C_1$–$C_4$ alkyl and $C_1$–$C_4$ alkoxy, and the halo substituents may be chloro or fluoro. Most preferably, $R_1$ is the group —C(O)W, W being the group —$OR_4$, wherein $R_4$ is a $C_1$–$C_3$ alkyl.

$R_2$ and each $R_3$ in graphic formula I may be hydrogen, $C_1$–$C_6$ alkyl, $C_3$–$C_7$ cycloalkyl, substituted or unsubstituted phenyl, the group —$OR_7$, wherein $R_7$ is hydrogen, ($C_1$–$C_6$)alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, ($C_1$–$C_6$)alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ haloalkyl, allyl, and the group, —$CH(R_8)X$, wherein X is CN, $CF_3$, halogen or —C(O)W and $R_8$ is hydrogen or $C_1$–$C_6$ alkyl; or $R_7$ is the group, —C(O)Y, wherein Y is hydrogen, $C_1$–$C_6$ alkyl, $C_1$–$C_6$ alkoxy, the substituted or unsubstituted aryl groups phenyl or naphthyl, phenoxy, $C_1$–$C_6$ mono- or di-alkyl substituted phenoxy, $C_1$–$C_6$ mono- or di-alkoxy substituted phenoxy, $C_1$–$C_6$ alkylamino, phenylamino, $C_1$–$C_6$ mono- or di-alkyl substituted phenylamino, or $C_1$–$C_6$ mono- or di-alkoxy substituted phenylamino, said aryl, e.g., phenyl, substituents being selected from $C_1$–$C_6$ alkyl or $C_1$–$C_6$ alkoxy, said halogen or halo substituents are chloro or fluoro and n is selected from the integers 0, 1, 2, and 3. Preferably, $R_2$ and each $R_3$ are hydrogen, $C_1$–$C_3$ alkyl, $C_3$–$C_5$ cycloalkyl substituted or unsubstituted phenyl or —$OR_7$, wherein $R_7$ is hydrogen, ($C_1$—$C_3$)alkyl, or the group, —$CH(R_8)X$, wherein X is CN or —C(O)W and $R_8$ is hydrogen or methyl; or $R_7$ is the group —C(O)Y wherein Y is $C_1$–$C_3$ alkyl or $C_1$–$C_3$ alkoxy, said phenyl substituents being $C_1$–$C_3$ alkyl or $C_1$–$C_3$ alkoxy and n is selected from the integers 0 and 1. In the definitions of $R_1$, $R_2$ and $R_3$ in graphic formula I, like letters have the same meaning unless stated otherwise.

B and B' in graphic formula I may each be selected from the group consisting of: (i) the substituted or unsubstituted aryl groups phenyl and naphthyl; (ii) the substituted or unsubstituted heterocyclic aromatic groups pyridyl, furanyl, benzofuranyl, thienyl, and benzothienyl, said aryl and heterocyclic substituents being selected from the group consisting of hydroxy, $C_1$–$C_6$ alkyl, $C_1$–$C_6$ haloalkyl, $C_1$–$C_6$ alkoxy, ($C_1$–$C_6$)alkoxy($C_1$–$C_4$)alkyl, acryloxy, methacryloxy and halogen, said halogen or (halo) groups being fluoro or chloro; (iii) the groups represented by the following graphic formulae II A and II B:

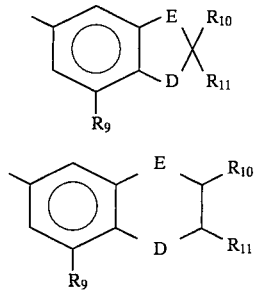

wherein D may be oxygen or substituted nitrogen and E may be carbon or oxygen, provided that when D is substituted nitrogen, E is carbon, said nitrogen substituents being selected from the group consisting of hydrogen, $C_1$–$C_6$ alkyl, and $C_1$–$C_5$ alkyl carbonyl. $R_{10}$ and $R_{11}$ in graphic formulae IIA and IIB may be hydrogen or $C_1$–$C_6$ alkyl and $R_9$ may be hydrogen, $C_1$–$C_6$ alkyl and $C_1$–$C_6$ alkoxy, hydroxy, or halogen, said halogen being selected from chloro or fluoro; (iv) $C_1$–$C_6$ alkyl, $C_1$–$C_6$ haloalkyl, ($C_1$–$C_6$)alkoxy ($C_1$–$C_4$ )alkyl, $C_3$–$C_6$ cycloalkyl, mono($C_1$–$C_6$)alkoxy ($C_3$–$C_6$)cycloalkyl, and halo($C_3$–$C_6$)cycloalkyl, said halo group being selected from fluoro or chloro; and (v) B and B' taken together may form the saturated bicyclic ring compounds selected from the group consisting of adamantylidene, bornylidene, and norbornylidene.

Preferably, B and B' are each selected from the group consisting of: (i) substituted or unsubstituted phenyl, said phenyl substituents being selected from the group consisting of $C_1$–$C_3$ alkyl, and $C_1$–$C_3$ alkoxy; (ii) the groups represented by graphic formulae II A and II B, wherein D is oxygen and E is carbon; $R_{10}$ and $R_{11}$ are each hydrogen or $C_1$–$C_3$ alkyl; and $R_9$ is a hydrogen; (iii) $C_1$–$C_4$ alkyl; and (iv) B and B' taken together form the saturated bicyclic ring compound adamantylidene.

Compounds represented by graphic formula I may be prepared by the following steps. In Reaction A shown below, compounds represented by graphic formula V or VA are either purchased or prepared by Friedel-Crafts methods using an appropriately substituted or unsubstituted benzoyl chloride of graphic formula IV with a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent potential phenyl substituents.

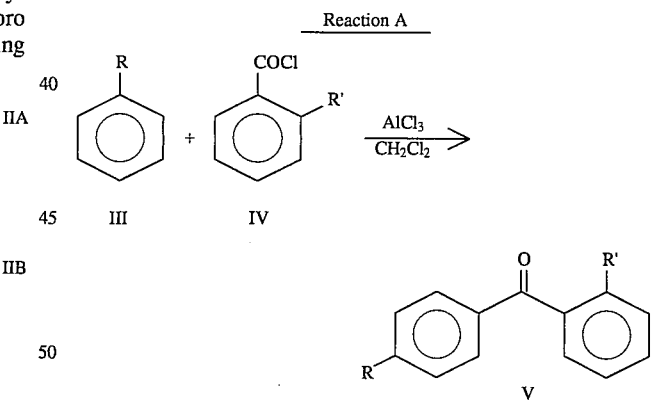

In reaction B, the substituted or unsubstituted ketone is represented by graphic formula VA, in which B and B' may represent groups other than substituted or unsubstituted phenyl, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound.

Reaction B

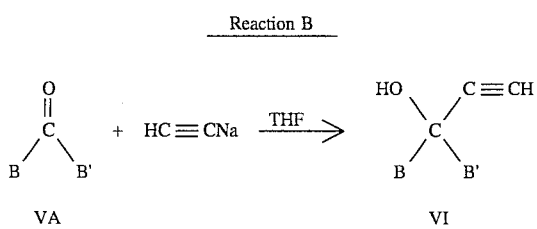

In reaction C, 1,4-dihydroxy-2-naphthoic acid, represented by graphic formula VII, is reacted with R" halide, e.g., methyl iodide, ethyl halide, benzyl bromide, etc., in the presence of ethyldiisopropyl amine in a suitable solvent such as anhydrous dimethylformamide (DMF), to form the corresponding 1,4-dihydroxy-2-naphthoate, which is represented by graphic formula VIII. This reaction is further described in *The Journal of Organic Chemistry*, 46(17), 1981, page 3477.

In reaction D, a substituted or unsubstituted acetophenone, benzophenone, or benzaldehyde represented by graphic formula IX is reacted with dimethyl succinate (graphic formula X) in the presence of a base such as sodium hydride or a potassium t-butoxide in a suitable solvent such as toluene to form the appropriate substituted monoester of an α-arylidene succinic acid, represented by graphic formula XI. Other substituents on the compound represented by graphic formula XI may be prepared by using different succinate esters, such as diethyl succinate. Compound XI is heated with acetic anhydride and anhydrous sodium acetate to form the corresponding acetate derivative represented by the graphic formula XII. Compound XII is reacted with hydrochloric acid and an anhydrous alcohol such as anhydrous methanol to form the corresponding naphthol, represented by graphic formula XIII (or XIIIA in Reaction E). Reaction D is further described in the text *Organic Reactions*, Vol. VI, Chapter 1, pages 1–73, John Wiley & Sons, Inc., New York.

Reaction D

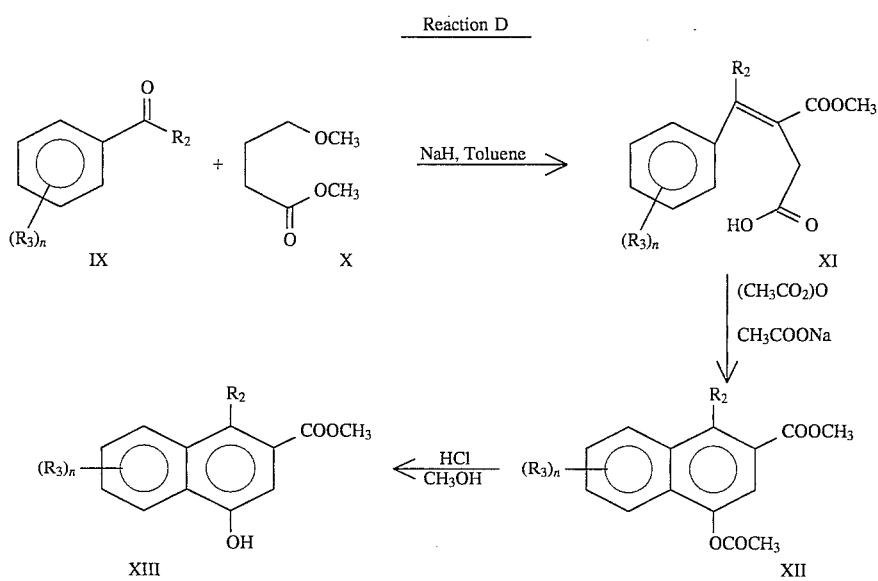

Reaction C

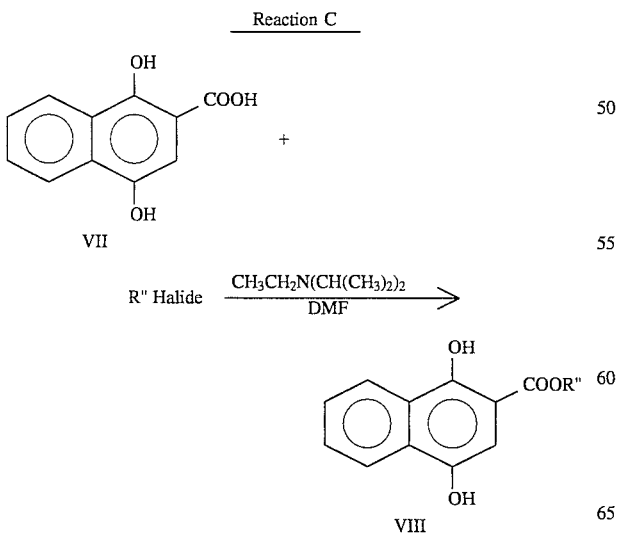

In Reaction E, the propargyl alcohol represented by graphic formula VI is coupled with the naphthol represented by graphic formula XIII A to form compounds represented by graphic formula I. In graphic formula XIII A, the methoxycarbonyl group of graphic formula XIII is replaced with "$R_1$".

Reaction E

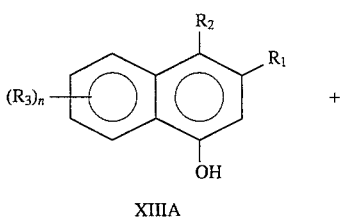

Reaction E

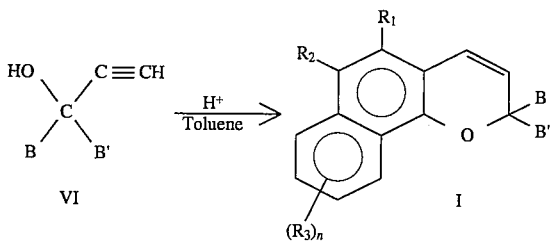

As shown in Reaction F, when $R_2$ in graphic formula I is —OH, this substituent can be converted to a variety of different groups by reacting such compound, as represented by graphic formula XIV, with acylating or alkylating agents. For example, Compound XIV may be reacted with methyl iodide (or other alkylating agent) in the presence of anhydrous potassium carbonate in a suitable solvent such as anhydrous acetone to form compounds represented by graphic formula XV, in which $R_2$ is a methoxy substitutent. Alkylating reactions are further described in "Organic Synthesis," Vol. 31, pages 90–93, John Wiley & Sons, Inc., New York, N.Y. Alternatively, Compound XIV may be reacted with acetyl chloride (or other acylating agent) in the presence of triethylamine in an appropriate solvent, such as methylene chloride, to form compounds represented by the graphic formula XVI, in which $R_2$ is an acetoxy substitutent. Acylating reactions are further described in "Organic Synthesis," Vol. 32, pages 72–77, John Wiley & Sons, Inc., New York, N.Y.

Reaction F

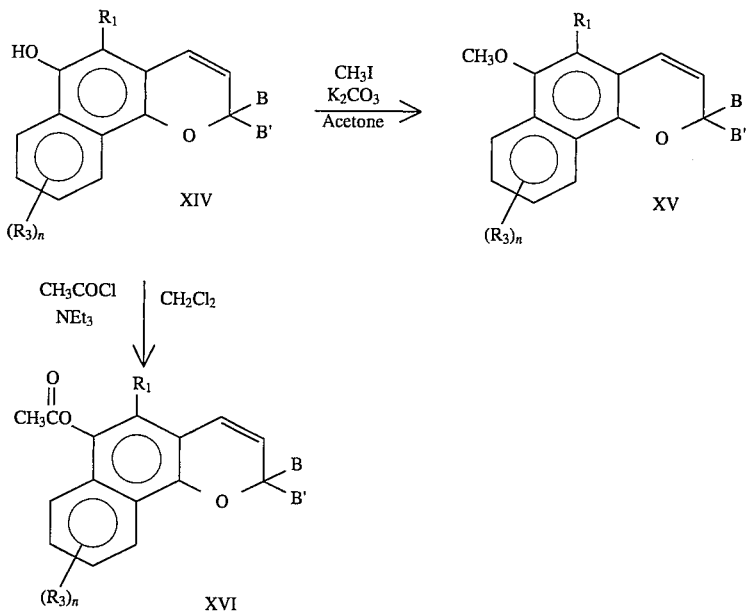

Compounds represented by graphic formula I may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit color changes from colorless to colors ranging from yellow to red/purple.

Examples of contemplated naphthopyrans within the scope of the invention are the following:

(a) 2,2-Bis(4-methoxyphenyl)-5-methoxycarbonyl-6-hydroxy-[2H]-naphtho[1,2-b]pyran;

(b) 2,2-Bis(4-methoxyphenyl)-5-methoxycarbonyl-6-methoxy-[2H]-naphtho[1,2-b]pyran;

(c) 2,2-Bis(4-methoxyphenyl)-5-methoxycarbonyl-6-(ethoxycarbonyl) methoxy-[2H]-naphtho[1,2-b]pyran;

(d) 2-(4-Methoxyphenyl)-2-t-butyl-5-methoxycarbonyl-6-acetoxy-[2H]-naphtho[1,2-b]pyran;

(e) 2-(4-Methoxyphenyl)-2-phenyl-5-methoxycarbonyl-6-(cyanomethoxy)-[2H]-naphtho[1,2-b]pyran;

(f) 2,2-Bis(4-methylphenyl)-5-methoxycarbonyl-6-(methoxycarbonyloxy)-[2H]-naphtho[1,2-b]pyran;

(g) 2,2-Diphenyl-5-methoxycarbonyl-6-acetoxy-[2H]-naphtho[1,2-b]pyran;

(h) 2,2-Bis(4-methoxyphenyl)-5-methoxycarbonyl-6-methyl-[2H]-naphtho[1,2-b]pyran;

(i) 2,2-Bis(4-methoxyphenyl)-5-methoxycarbonyl-6-methyl-9-methoxy-[2H]-naphtho[1,2-b]pyran;

(j) 2,2-Diphenyl-5-methoxycarbonyl-6-propionyloxy-[2H]-naphtho[1,2-b]pyran;

(k) 2,2-Bis(3-trifluoromethylphenyl)-5-methoxycarbonyl-6-acetoxy-[2H]-naphtho[1,2-b]pyran;

(l) 2-(4-Methoxyphenyl)-2-(2-methyl-2,3-dihydrobenzofuran-5-yl)-5-methoxycarbonyl-6(ethoxycarbonyl)-methoxy-[2H]-naphtho[1,2-b]pyran; and (m) 2,2'Spiroadamantylene-5-methoxycarbonyl-6-methoxy-[2H]-naphtho[1,2-b]pyran.

Commercially available photoreactive inorganic glass lenses containing silver halide particles darken to a neutral gray or brown color in sunlight. In order to duplicate this color change in a plastic lens using the organic photochromic naphthopyrans of the present invention, it is contemplated that such naphthopyrans be used in combination with other appropriate complementary organic photochromic materials so that together they produce the desired gray or brown color shade when the plastic lens containing such photochromic materials is exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue color compound.

A first group of organic photochromic compounds contemplated for use as complementary photochromic materials are those having an activated absorption maximum within the visible range of greater than 590 nanometers, e.g., between about greater than 590 to 700 nanometers. These materials typically exhibit a blue, blueish-green, or blueish-purple color when exposed to ultraviolet light in an appropriate solvent or matrix. Many of such compounds are described in the open literature. For example, spiro(indoline)naphthoxazines have been described, among others, in U.S. Pat. Nos. 3,562,172; 3,578,602; 4,215,010; and 4,342,668. Spiro(indoline)naphthoxazines having certain substituents on the 8' and 9' positions of the naphthoxazine portion of the molecule, such as 1,3,3-trimethyl-5-methoxy-9'-methoxycarbonyl-8'-acetoxy spiro[indoline-2-3'-[3H]naphth-[2,1b]-[1,4]oxazine, are the subject of co-pending U.S. patent application Ser. No. 07/993,587, filed Dec. 21, 1992. Spiro(indoline)pyridobenzoxazines are described in U.S. Pat. No. 4,637,698. Spiro(benzindoline)pyridobenzoxazines and spiro(benzindoline)naphthoxazines are described in U.S. Pat. No. 4,931,219. Spiro(benzindoline)naphthopyrans are described in Japanese Patent Publication 62/195383. Spiro(indoline)benzoxazines are described in U.S. Pat. No. 4,816,584. Spiro(indoline)benzopyrans, spiro(indoline)naphthopyrans and spiro(indoline)quinopyrans are described, for example, in U.S. Pat. No. 4,880,667. Benzopyrans and naphthopyrans having a nitrogen-containing substituent in the 2-position of the pyran ring are described in U.S. Pat. No. 4,818,096. Spiro(indoline)pyrans are also described in the text, *Techniques in Chemistry*, Volume III, "Photochromism," Chapter 3, Glenn H. Brown, Editor, John Wiley and Sons, Inc., New York, 1971.

A second group of organic photochromic substances contemplated for use as complementary photochromic compounds are those having at least one absorption maximum and preferably two absorption maxima within the visible range of between about 400 and less than 550 nanometers. These materials typically exhibit a yellow to red/purple color when exposed to ultraviolet light in an appropriate solvent or matrix. Such compounds include certain chromenes, i.e., benzopyrans and 3H-naphtho[2,1-b]pyrans, many of which are described in the open literature, e.g., U.S. Pat. Nos. 3,567,605; 4,826,977; and 5,066,818. Examples of benzopyrans 5 and naphthopyrans having a spiroadamantane group in the 2-position of the ring are described in U.S. Pat. No. 4,826,977. Naphthopyrans, i.e., 3H-naphtho[2,1-b] pyrans, having at least one ortho-substituted phenyl substituent at the 3-position of the pyran ring are described in U.S. Pat. No. 5,066,818. Naphthopyran compounds having certain substituents at the number 8 carbon atom and certain substituents at the number 7 or 9 carbon atom, all substituents being on the naphtho portion of the naphthopyran, are the subject of co-pending U.S. patent application Ser. No. 08/080,246, filed Jun. 21, 1993. Naphthopyrans substituted at the 3 position of the pyran ring with (i) an aryl substituent and (ii) a phenyl substituent having a 5- or 6-member heterocyclic ring fused at the number 3 and 4 carbon atoms of the phenyl substituent are the subject of co-pending U.S. patent application Ser. No. 08/080,250 filed Jun. 21, 1993. Naphthopyran compounds substituted at the number 8 carbon atom on the naphtho portion of the naphthopyran ring, with for example, a methoxy group are the subject of U.S. Pat. No. 5,238,931. Naphthopyran compounds, examples of which are 3-aryl-3-arylalkenyl naphthophyrans, are the subject of U.S. Pat. No. 5,274,132.

A third group of organic photochromic substances contemplated for use as complementary photochromic compounds are those having an absorption maximum within the visible range of between about 400 to about 500 nanometers and another absorption maximum within the visible range of between about 500 to about 700 nanometers. These materials typically exhibit color(s) ranging from yellow/brown to purple/gray when exposed to ultraviolet light in an appropriate solvent or matrix. Examples of these compounds include certain benzopyran compounds, such as those having substituents at the 2-position of the pyran ring and a substituted or unsubstituted heterocyclic ring, such as a benzothieno or benzofurano ring fused to the benz portion of the benzopyran. Such materials are the subject of co-pending U.S. patent application Ser. No. 08/304,970, filed Sep. 13, 1994.

The disclosures of such photochromic compounds in the aforedescribed patents and patent applications are incorporated herein, in toro, by reference. Photochromic articles containing a naphthopyran(s) of the present invention may contain also one of the aforesaid complementary photochromic compounds or a mixture of such photochromic compounds, as desired. Mixtures of photochromic compounds may be used to attain certain activated colors such as a near neutral gray or brown.

The novel substituted 2H-naphtho(1,2-b)pyran organic photochromic compounds of the present invention may be described as photochromic compounds that exhibit activated colors of from yellow to red/purple, and therefore may be used in place of or in combination with the aforesaid second group of photochromic compounds. The compounds of the present invention (hereinafter referred to as a second group photochromic compound) may be combined with or used in conjunction with the first group of photochromic compounds that color to purple/blue, e.g., the spirooxazine-type compounds, or with other photochromic substances in the aforesaid second group of photochromic compounds. Either members of the first or second group of photochromic compounds or mixtures of such compounds may be combined with or used in conjunction with the third group of described organic photochromic compounds that color from yellow/brown to purple/gray. Each of the photochromic compounds or substances containing same described herein may be used in amounts and in a ratio such that an organic host material to which the mixture of compounds is applied or in which they are incorporated exhibits a desired resultant color, e.g., a substantially neutral color such as shades of gray or brown, when activated with unfiltered sunlight, i.e., as near a neutral color as possible given the colors of the activated photochromic compounds. The relative amounts of the aforesaid photochromic compounds used will vary and depend in part upon the relative intensities of the color of the activated species of such compounds, and the ultimate color desired. Generally, the weight ratio of the aforedescribed organic photochromic compound combinations, i.e., (first to second), (first to third), and (second to third), will vary from about 1:3 to about 3:1, e.g., between about 0.75:1 and about 2:1. The combination of the first, second, and third organic photochromic compounds may have a weight ratio that will vary from about 1:3:1 to 3:1:3.

A near neutral gray color exhibits a spectrum that has relatively equal absorption in the visible range between 400 and 700 nanometers, e.g., between 440 and 660 nanometers. A near neutral brown color exhibits a spectrum in which the absorption in the 440–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, New York (1981). As used in the specification, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The photochromic compounds of the present invention may be applied to or incorporated into a host material by various methods described in the art. Such methods include dissolving or dispersing the compound within the host material, e.g., imbibition of the photochromic compound into the host material by immersion of the host material in a hot solution of the photochromic compound or by thermal transfer; providing the photochromic compound as a separate layer between adjacent layers of the host material, e.g., as a part of a polymeric film; and applying the photochromic compound as part of a coating placed on the surface of the host material. The term "imbibition" or "imbibe" is intended to mean and include permeation of the photochromic substance alone into the host material, solvent assisted transfer, absorption of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The polymeric host material will usually be transparent, but may be translucent or even opaque. The polymeric product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material, e.g., materials suitable for optical applications, such as plano and vision correcting ophthalmic lenses, windows, automotive transparencies, e.g., windshields, aircraft transparencies, plastic sheeting, polymeric films, etc.

Examples of host materials which may be used with the photochromic substances or compositions described herein include: polymers, i.e., homopolymers and copolymers, of polyol(allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, polyesters, poly(ethylene terephthalate), polystyrene, copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. No. 4,360,653 and 4,994,208; and copolymers with aliphatic urethanes, the terminal portion of which contain allyl or acrylyl functional groups as described in U.S. Pat. No. 5,200,485; cellulose acetate, cellulose propionate, cellulose butyrate, cellulose acetate butyrate, polystyrene and copolymers of styrene with methyl methacrylate, vinyl acetate and acrylonitrile.

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity. Generally, the amount of total photochromic substance incorporated into or applied to a photochromic optical host material may range from about 0.15 to about 0.35 milligrams per square centimeter of surface to which the photochromic substance(s) is incorporated or applied.

The present invention is more particularly described in the following examples which are intended as illustrative only, since numerous modifications and variations therein will be apparent to those skilled in the art.

EXAMPLE 1

STEP 1

4,4'-dimethoxybenzophenone (0.27 moles) was dissolved in a reaction flask containing 200 milliliters (ml) of anhydrous tetrahydrofuran saturated with acetylene and stirred at room temperature. An 18 weight percent suspension of sodium acetylide in xylene/mineral oil (0.3 mole of sodium acetylide) was added to the reaction flask and the mixture was stirred. After stirring 16 hours at room temperature under a nitrogen atmosphere, the contents of the reaction flask mixture was added to a 5 weight percent aqueous hydrochloric acid and ice mixture. The resulting mixture was extracted with diethyl ether. The organic layer was separated, washed, and dried over anhydrous sodium sulfate. The solvents, diethyl ether and tetrahydrofuran, were removed under vacuum to yield an oily product containing 1,1-bis(4-methoxyphenyl)-2-propyn-1-ol, which was not purified further but used directly in the next step.

STEP 2

1,1-bis(4-methoxyphenyl)-2-propyn-1-ol (about 0.025 mole) from Step 1 and methyl-1,4-dihydroxy-2-naphthoate (5 gm., 0.022 mole) were added to a reaction flask containing 200 ml of toluene and stirred. A catalytic amount of p-toluene-sulfonic acid (about 100 milligrams) was added, and the mixture was stirred for 4 hours. Afterwards, the reaction mixture was poured into a 10 weight percent sodium hydroxide solution. The organic layer was separated, washed with water, and dried over anhydrous sodium sulfate. The remaining solvent, toluene, was removed under vacuum. The resulting oil was purified using a silica gel column and a 1:3 mixture of chloroform:hexane as the eluant. The photochromic fractions were combined and the eluent was removed under vacuum. The resulting product was induced to crystallize from hexane. The recovered product had a melting point of 160° C. A nuclear magnetic resonance (NMR) spectrum showed the product to have a structure consistent with 2,2-bis(4-methoxyphenyl)-5-methoxycarbonyl-6-hydroxy-[2H]-naphtho[1,2-b]pyran.

EXAMPLE 2

2,2-bis(4-methoxyphenyl)-5-methoxycarbonyl-6-hydroxy-[2H]-naphtho[1,2-b]pyran (2 grams) prepared as described in Example 1, anhydrous potassium carbonate (2 grams), and methyliodide (2 grams) were added to a reaction flask containing 40 milliliters of anhydrous acetone, stirred and refluxed under an argon atmosphere. Afterwards, the acetone was removed under vacuum and 25 milliliters each of water and methylene chloride were added to the reaction mixture. The mixture was stirred for 30 minutes and the organic layer was separated, washed, and dried. The remaining solvent, methylene chloride, was removed under vacuum. The resulting oily concentrate was crystallized from a 1:1 hexane:diethyl ether mixture. The solid obtained was suction filtered, washed with hexane and air dried. The resulting product had a melting point of 175°–177° C. A nuclear magnetic resonance (NMR) spectrum showed the product to have a structure consistent with 2,2-bis(4-methoxyphenyl)-5-methoxycarbonyl-6-methoxy-[2H]-naphtho[1,2-b]pyran.

EXAMPLE 3

The procedure of Example 2 was followed except that ethyl bromoacetate was used in place of methyl iodide. The resulting product had a melting point of 123° C. A nuclear magnetic resonance (NMR) spectrum showed the product to have a structure consistent with 2,2-bis(4-methoxyphenyl)-5-methoxycarbonyl-6-ethoxycarbonylmethoxy-[2H]-naphtho[1,2-b]pyran.

EXAMPLE 4

STEP 1

The procedure of Step 1 of Example 1 was followed except that 1-(4-methoxyphenyl)-2,2-dimethyl-1-propanone was used in place of 4,4-dimethoxybenzophenone to produce 3-(4-methoxyphenyl)-4,4-dimethyl-1-pentyn-3-ol.

STEP 2

The procedure of Step 2 of Example 1 was followed except that 3-(4-methoxyphenyl)-4,4-dimethyl-1-pentyn-3-ol was used in place of 1,1-bis(4-methoxyphenyl)-2-propyn-1-ol to produce 2-(4-methoxyphenyl)-2-t-butyl-5-methoxycarbonyl-6-hydroxy-[2H]-naphtho[1,2-b]pyran.

STEP 3

2-(4-methoxyphenyl)-2-t-butyl-5-methoxycarbonyl-6-hydroxy-[2H]-naphtho[1,2-b]pyran (2 grams), prepared as described above in Step 2, and triethylamine (2 grams) were added to a reaction flask containing 50 milliliters of anhydrous methylene chloride and stirred. Acetyl chloride (2 grams) was added to the reaction flask and the reaction mixture was stirred for 1 hour. Distilled water (50 milliliters) was added to the reaction flask and the reaction mixture was stirred for another half hour. Afterwards, the organic layer was separated, washed and dried over anhydrous sodium sulfate. Evaporation of solvent resulted in an oily residue that was crystallized from a 1:1 hexane:diethyl ether mixture. The solid was suction filtered, washed with hexane, and air dried. The resulting product had a melting point of 152°–159° C. A nuclear magnetic resonance (NMR) spectrum showed the product to have a structure consistent with 2-(4-methoxyphenyl)-2-t-butyl-5-methoxycarbonyl-6-acetoxy-[2]-naphtho[1,2-b]pyran.

EXAMPLE 5

STEP 1

The procedure of Step 1 of Example 1 was followed except that 4-methoxybenzophenone was used in place of 4,4-dimethoxybenzophenone to produce 1-(4-methoxyphenyl)-1-phenyl-2-propyn-1-ol.

STEP 2

The procedure of Step 2 of Example 1 was followed except that 1-(4-methoxyphenyl)-1-phenyl-2-propyn-1-ol was used in place of 1,1-bis(4-methoxyphenyl)-2-propyn-1-ol to produce 2-(4-methoxyphenyl)-2-phenyl-5-methoxycarbonyl-6-hydroxy-[2H]-naphtho[1,2-b]pyran.

STEP 3

The procedure of Example 3 was followed except that 2-(4-methoxyphenyl)-2-phenyl-5-methoxycarbonyl-6-hydroxy-[2H]-naphtho[1,2-b]pyran was used in place of 2,2- bis(4-methoxyphenyl)-5-methoxycarbonyl-6-hydroxy-[2H]-naphtho[1,2-b]pyran and bromoacetonitrile was used in place of ethyl bromoacetate. The resulting product had a melting point of 125° C. A nuclear magnetic resonance (NMR) spectrum showed the product to have a structure consistent with 2-(4-methoxyphenyl)-2-phenyl-5-methoxycarbonyl-6-(cyanomethoxy)-[2H]-naphtho[1,2-b]pyran.

EXAMPLE 6

STEP 1

The procedure of Step 1 of Example 1 was followed except that 4,4'-dimethylbenzophenone was used n place of 4,4'-dimethoxybenzophenone to produce 1,1-bis(4-methylphenyl)-2-propyn-1-ol.

STEP 2

The procedure of Step 2 of Example 1 was followed except that 1,1-bis(4-methylphenyl)-2-propyn-1-ol was used in place of 1,1-bis(4-methoxyphenyl)-2-propyn-1-ol to produce 2,2-bis(4-methylphenyl)-5-methoxycarbonyl-6-hydroxy-[2H]-naphtho [1,2-b]pyran.

STEP 3

The procedure of Example 3 was followed except that 2,2-bis(4-methylphenyl)-5-methoxycarbonyl-6-hydroxy-[2H]-naphtho[1,2-b]pyran was used in place of 2,2-bis(4-methoxyphenyl)-5-methoxycarbonyl-6-hydroxy-[2H]-naphtho[1,2-b]pyran and methyl chloroformate was used in place of bromoethyl acetate. The resulting product had a melting point of 166° C. A nuclear magnetic resonance (NMR) spectrum showed the product to have a structure consistent with 2,2-bis(4-methylphenyl)-5-methoxycarbonyl-6-(methoxycarbonyloxy)-[1,2-b]pyran.

EXAMPLE 7

STEP 1

The procedure of Step 2 of Example 1 was followed except that 1,1-diphenyl-2-propyn-1-ol was used in place of 1,1-bis (4-methoxyphenyl)-2-propyn-1-ol to produce 2,2-diphenyl-5-methoxycarbonyl-6-hydroxy-[2H]-naphtho[1,2-b]pyran.

STEP 2

The procedure of Step 3 of Example 4 was followed except that 2,2-diphenyl-5-methoxycarbonyl-6-hydroxy-[2H]-naphtho[1,2-b]pyran was used in place of 2-(4-methoxyphenyl)-2-t-butyl-5-methoxycarbonyl-6-hydroxy-[2H]-naphtho[1,2-b]-pyran. The resulting product had a melting point of 190°–192° C. A nuclear magnetic resonance (NMR) spectrum showed the product to have a structure consistent with 2,2-diphenyl-5-methoxycarbonyl-6-acetoxy-[2H]-naphtho[1,2-b]pyran.

EXAMPLE 8

The procedure of Step 2 of Example 1 was followed except that methyl-4-hydroxy, 1-methyl-2-naphthoate was used in place of methyl-4-dihydroxy-2-naphthoate. The resulting product had a melting point of 175°–176° C. A nuclear magnetic resonance (NMR) spectrum showed the product to have a structure consistent with 2,2-bis(4-methoxyphenyl)-5-methoxycarbonyl-6-methyl-[2H]-naphtho[1,2-b]pyran.

EXAMPLE 9

The procedure of Step 2 of Example 1 was followed except that methyl-4-hydroxy-6-methoxy-1-methyl-2-naphthoate was used in place of methyl-4-dihydroxy-2-naphthoate. The resulting product had a melting point of 132°–133° C. A nuclear magnetic resonance (NMR) spectrum showed the product to have a structure consistent with 2,2-bis(4-methoxyphenyl)-5-methoxycarbonyl-6-methyl-9-methoxy-[2H]-naphtho[1,2-b]pyran.

EXAMPLE 10

The procedure of Example 7 was followed except that in step 2, isobutyryl chloride was used in place of acetyl chloride. The resulting product had a melting point of 173° C. A nuclear magnetic resonance (NMR) spectrum showed the product to have a structure consistent with 2,2-diphenyl-5-methoxycarbonyl-6-(propionyloxy)-[2H]-naphtho[1,2-b]pyran.

EXAMPLE 11

STEP 1

The procedure of Step 1 of Example 1 was followed except that 3,3-bis(trifluoromethyl)benzophenone was used in place of 4,4'-dimethoxybenzophenone to produce 1,1-bis(3-trifluoro-methylphenyl)-2-propyn-1-ol.

STEP 2

The procedure of Step 2 of Example 1 was followed except that 1,1-bis(3-trifluoromethylphenyl)-2-propyn-1-ol was used in place of 1,1-bis(4-methoxyphenyl)-2-propyn-1-ol to produce 2,2-bis(3-trifluoromethylphenyl)-5-methoxycarbonyl-6-hydroxy[2H]-naphtho[1,2-b]pyran.

STEP 3

The procedure of Step 3 of Example 4 was followed except that 2,2-bis(3-trifluoromethylphenyl)-5-methoxycarbonyl-6-hydroxy-[2H]-naphtho[1,2-b]pyran was used used in place of 2-(4-methoxyphenyl)-2-t-butyl-5-methoxycarbonyl-6-hydroxy-[2H]-naphtho[1,2-b]pyran. The resulting product had a melting point of 160° C. A nuclear magnetic resonance (NMR) spectrum showed the product to have a structure consistent with 2,2-bis(3-trifluoromethylphenyl)-5-methoxycarbonyl-6-acetoxy-[2H]-naphtho[1,2-b]pyran.

EXAMPLE 2

STEP 1

The procedure of Step 1 of Example 1 was followed except that 5-(4-methoxybenzoyl)-2-methyl-2,3-dihydrobenzofuran was used in place of 4,4'-dimethoxybenzophenone to produce 1-(4-methoxyphenyl)-1-(2-methyl-2,3-dihydrobenzofur-5-yl)-2-propyn-1-ol.

STEP 2

The procedure of Step 2 of Example 1 was followed except that 1-(4-methoxyphenyl)-1-(2,3-dihydrobenzofur-5-yl)-2-propyn-1-ol was used in place of 1,1-bis(4-methoxyphenyl)-2-propyn-1-ol to produce 2-(4-methoxyphenyl)-2-(2-methyl-2,3-dihydrobenzofur-5-yl)-5-methoxycarbonyl-6-hydroxy-[2H]-naphtho[1,2-b]pyran.

STEP 3

The procedure of Example 3 was followed except that 2-(4-methoxyphenyl)-2-(2-methyl-2,3-dihydrobenzofur-5-yl)-5-methoxycarbonyl-6-hydroxy-[2H]-naphtho[1,2-b]pyran was used in place of 2,2-bis(4-methoxyphenyl)-5-methoxycarbonyl-6-hydroxy-[2H]-naphtho[1,2-b]pyran and ethyl bromoacetate was used in place of methyl iodide. The resulting product had a melting point of 130°–131° C. A nuclear magnetic resonance (NMR) spectrum showed the product to have a structure consistent with 2-(4-methoxyphenyl)-2-(2-methyl-2,3-dihydrobenzofur-5-yl)-5-methoxycarbonyl-6-ethoxycarbonylmethoxy-[2H]-naphtho[1,2-b]pyran.

EXAMPLE 13

STEP 1

The procedure of Step 1 of Example 1 was followed except that adamantanone was used in place of 4,4'-dimethoxy-benzophenone to produce 2-ethinyl-2-hydroxyadamantane.

STEP 2

The procedure of Step 2 of Example 1 was followed except that 2-ethinyl-2-hydroxyadamantane was used in place of 1,1-bis(4-methoxyphenyl)-2-propyn-1-ol to produce 2,2-spiro-adamantylene-5-methoxycarbonyl-6-hydroxy-[2H]-naphtho[1,2-b]pyran.

STEP 3

The procedure of Example 2 was followed except that 2,2-spiroadamantylene-5-methoxycarbonyl-6-hydroxy-[2H]-naphtho[1,2-b]pyran was used in place of 2,2-bis(4-methoxyphenyl)-5-methoxycarbonyl-6-hydroxy-[2H]-naphtho[1,2-b]pyran. The resulting product had a melting point of 130°–131° C. A nuclear magnetic resonance (NMR) spectrum showed the product to have a structure consistent with 2,2'-spiro-adamantylene-5-methoxycarbonyl-6-methoxy-[2H]-naphtho[1,2-b] pyran.

Comparative Example 1

The procedure of Step 2 of Example 1 was followed except that 1,1-diphenyl-2-propyn-1-ol was used in place of 1,1-bis(4-methoxyphenyl)-2-propyn-1-ol and 1-hydroxynaphthalene was used in place of methyl-4-dihydroxy-2-naphthoate to produce 2,2-diphenyl-[2H]-naphtho[1,2-b]pyran.

Comparative Example 2

The procedure of Step 2 of Example 1 was followed except that 1,1-diphenyl-2-propyn-1-ol was used in place of 1,1-bis(4-methoxyphenyl)-2-propyn-1-ol and 3-methyl-1-hydroxynaphthalene was used in place of methyl,1,4-dihydroxy-2-naphthoate to produce 2,2-diphenyl-5-methyl-[2H]-naphtho[1,2-b]pyran.

Comparative Example 3

The procedure of Step 2 of Example 1 was followed except that 2-ethinyl-2-hydroxyadamantane was used in place of 1,1-bis(4-methoxyphenyl)-2-propyn-1-ol and 1-hydroxynaphthalene was used in place of methyl 1,4-dihydroxy-2-naphthoate to produce 2,2-spiroadamantylene-[2H]-naphtho[1,2-b]pyran.

Comparative Example 4

The procedure of Example 4 was followed except that in step 2,1-hydroxynaphthalene was used in the place of methyl 1-4-dihydroxy-2-naphthoate to produce 2-(4-methoxyphenyl)-2-t-butyl-[2H] naphtho[1,2-b]pyran.

Example 14

Part A

Testing was done with selected photochromic naphthopyrans incorporated into test square polymerizates by one of two different imbibition processes. The test square polymerizates were prepared from a diethylene glycol bis(allyl carbonate) composition and measured ⅛ inch (0.3 centimeters)×2 inches (5.1 centimeters)×2 inches (5.1 centimeters). In one of the imbibition processes, the photochromic naphthopyran was dissolved to form a 10 weight percent solution in a 1:9 mixture of ethyl cellulose:toluene. The solution was then spin coated onto the test squares and allowed to dry. Samples were then heated in a hot-air oven at 135°–155° C. for a period of time sufficient to thermally transfer the photochromic into the test squares. After cooling, the ethyl cellulose/toluene resin film was removed from the test squares by washing with acetone.

Alternatively, the test squares were imbibed by the following procedure. Each naphthopyran was dissolved into toluene to form a four (4) weight percent solution of the compound. A piece of No. 4 Whatman filter paper was saturated with the naphthopyran toluene solution and allowed to air dry. The dried filter paper was placed on one side of the test square. A piece of untreated filter paper was placed on the other side of the polymeric test square and the resulting sandwich was placed between two flat aluminum metal plates. The entire assembly was then placed in a 135°–155° C. oven for a time sufficient to thermally transfer the naphthopyran into the polymeric test square. After cooling, the test squares were washed with acetone. In both imbibition processes, the residence times in the oven for the test squares were adjusted to imbibe comparable amounts of the naphthopyran compounds. This was done in order to yield a comparable UV absorbance at the lambda max of the compound in the near UV.

Part B

The photochromic squares were tested for photochromic response rates on an optical bench. Prior to testing on the optical bench, the photochromic test squares were exposed to 365 nanometer ultraviolet light for about 15 minutes to activate the photochromic compounds and then placed into a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 75° F. (23.9° C.). The bench was fitted with a 150 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. A collimated beam of light from a tungsten lamp was passed through the square at a small angle normal to the square. After passing through the square, the light from the tungsten lamp was directed through a photopic filter attached to a detector. The photopic filter passes wavelengths such that the detector mimics the response of the human eye. The output signals from the detector(s) were processed by a radiometer.

Change in optical-density (ΔOD) was determined by inserting an imbibed square in the bleached state into the sample holder, adjusting the transmittance scale to 100%, opening the shutter from the Xenon lamp to provide ultraviolet radiation to change the imbibed square from the bleached state to an activated (i.e., darkened) state, measuring the transmittance in the activated state, and calculating the change in optical density according to the formula Δ OD=log(100/% Ta) where % Ta is the percent transmittance in the activated state and the logarithm is to the base The ΔOD/Min, which represents the sensitivity of the photochromic compound's response to UV light, was measured over the first five (5) seconds of UV exposure, then expressed on a per minute basis. The saturation optical density (OD) was taken under identical conditions as the ΔOD/Min, except UV exposure was continued for 20 minutes for the examples in Table 1. The lambda max reported in Table 1 is the wavelength in the visible spectrum at which the maximum absorption of the activated (colored) form of the photochromic compound in a diethylene glycol bis(allyl carbonate) composition occurs. The Bleach Rate (T1/2) is the time interval in seconds for the absorbance of the activated form of the naphthopyran in the test squares to reach one half the highest absorbance at room temperature (75° F., 23.9° C.) after removal of the source of activating light. Results for the Compounds of the Examples are tabulated in Table 1.

A comparison of Bleach Rate T 1/2 results for the Compounds of the Examples with the Compounds of the Comparative Examples having the same structure, except for the substituents at the 5 and 6 carbon position, is shown in Table 2.

The results of Table 1 show that each tested compound of the present invention has an acceptable bleach rate, i.e., fade rate; a high Δ OD at saturation, i.e., activated intensity; and a high coloration rate, i.e., sensitivity.

The results of Table 2 show in each comparison that the Compounds of the present invention have bleach rates that are much faster than the Compounds of the Comparative Examples.

The present invention has been described with reference to specific details of certain embodiments thereof, it is not intended that such details should be regarded as limitations upon the scope of the invention except insofar as they are included in the accompanying claims.

We claim:

1. A naphthopyran compound represented by the following graphic formula:

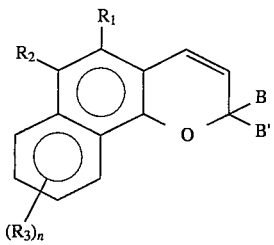

wherein, (a) $R_1$ is the group, —C(O)W, W being —$OR_4$ or —$N(R_5)R_6$, wherein $R_4$ is hydrogen, allyl, $C_1$–$C_6$ alkyl, phenyl, mono($C_1$–$C_6$)alkyl substituted phenyl, mono($C_1$–$C_6$)alkoxy substituted phenyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, ($C_1$–$C_6$)alkoxy($C_2$–$C_4$)alkyl, or

TABLE 1

Results for Compounds Imbibed into a Diethylene glycol bis-(allyl carbonate) composition

| COMPOUND EXAMPLE | LAMBDA MAX | Δ OD/Min SENSITIVITY | Δ OD @ SATURATION | BLEACH RATE T ½(SEC.) |
|---|---|---|---|---|
| 1 | 497 nm | 0.47 | 0.18 | 235 |
| 2 | 510 nm | 0.81 | 0.48 | 305 |
| 3 | 508 nm | 0.79 | 0.44 | 211 |
| 5 | 494 nm | — | — | — |
| 6 | 482 nm | 0.32 | 0.17 | 100 |
| 8 | 476 nm | 0.63 | 0.42 | 217 |
| 9 | 522 nm | 0.58 | 0.58 | 376 |
| 10 | 470 nm | 0.39 | 0.19 | 257 |
| 11 | 455 nm | 0.15 | 0.08 | 218 |
| 12 | 517 nm | 0.83 | 0.53 | 276 |

TABLE 2

Comparison of Bleach Rate (T ½ Results

| Compound Example | Bleach Rate T 1/2 (Sec.) |
|---|---|
| 7 | 220 |
| Comparative Example 1 | >1800 |
| Comparative Example 2 | 640 |
| 4 | 433 |
| Comparative Example 4 | >1800 |
| 13 | 98 |
| Comparative Example 3 | 225 |

$C_1$–$C_6$ haloalkyl, and wherein $R_5$ and $R_6$ are each selected from the group consisting of hydrogen, $C_1$–$C_6$ alkyl, $C_5$–$C_7$ cycloalkyl, phenyl, mono-substituted phenyl and di-substituted phenyl, said phenyl substituents being $C_1$–$C_6$ alkyl or $C_1$–$C_6$ alkoxy, and said halo substituents being chloro or fluoro;

(b) $R_2$ and each $R_3$ are hydrogen, $C_1$–$C_6$ alkyl, $C_3$–$C_7$ cycloalkyl, substituted or unsubstituted phenyl, the group —$OR_7$, wherein $R_7$ is hydrogen, ($C_1$–$C_6$)alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, ($C_1$–$C_6$)alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ haloalkyl, allyl, the group, —CH($R_8$)X, wherein X is CN, $CF_3$, halogen, or —C(O)W and $R_8$ is hydrogen or $C_1$–$C_6$ alkyl, or $R_7$ is the group, —C(O)Y, wherein Y is hydrogen, $C_1$–$C_6$ alkyl, $C_1$–$C_6$ alkoxy, the substituted or unsubstituted aryl groups phenyl or naphthyl, phenoxy, $C_1$–$C_6$ mono- or di-alkyl substituted phenoxy, $C_1$–$C_6$ mono-or di-alkoxy substituted phenoxy, $C_1$–$C_6$ alkylamino, phenylamino, $C_1$–$C_6$ mono- or di-alkyl substituted phenylamino, or $C_1$–$C_6$ mono- or di-alkoxy substituted phenylamino, said aryl substituents being selected from $C_1$–$C_6$ alkyl or $C_1$–$C_6$ alkoxy, said halogen or halo substituents being chloro or fluoro and n is selected from the integers 0, 1, 2, or 3; and (c) B and B' are each selected from the group consisting of:
 (i) the substituted or unsubstituted heterocyclic aromatic groups pyridyl, furanyl, benzofuranyl, thienyl, and benzothienyl, said heterocyclic substituents being selected from the group consisting of hydroxy, $C_1$–$C_6$ alkyl, $C_1$–$C_6$ haloalkyl, $C_1$–$C_6$ alkoxy, ($C_1$–$C_6$)alkoxy($C_1$–$C_4$)alkyl, acryloxy, methacryloxy and halogen, said halogen or (halo) groups being fluoro or chloro;
 (ii) the groups represented by the following graphic formulae:

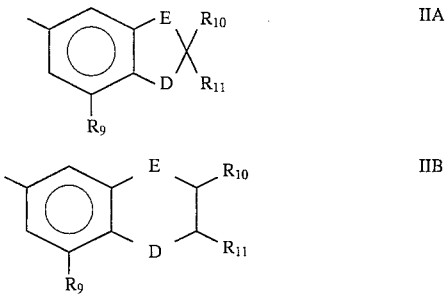

wherein D is oxygen or substituted nitrogen and E is carbon or oxygen, provided that when D is substituted nitrogen, E is carbon, said nitrogen substituents being selected from the group consisting of hydrogen, $C_1$–$C_6$ alkyl, and $C_1$–$C_5$ alkylcarbonyl; $R_{10}$ and $R_{11}$ are each hydrogen or $C_1$–$C_6$ alkyl; and $R_9$ is hydrogen, $C_1$–$C_6$ alkyl, $C_1$–$C_6$ alkoxy, hydroxy or halogen, said halogen being chloro or fluoro;
 (iii) $C_1$–$C_6$ alkyl, $C_1$–$C_6$ haloalkyl, ($C_1$–$C_6$) alkoxy($C_1$–$C_4$)alkyl, $C_3$–$C_6$ cycloalkyl, mono($C_1$–$C_6$) alkoxy($C_3$–$C_6$)cycloalkyl, and halo($C_3$–$C_6$)cycloalkyl, said halo group being fluorine or chlorine;
 (iv) the substituted or unsubstituted aryl groups phenyl and naphthyl, said aryl substituents being selected from the group consisting of hydroxy, $C_1$–$C_6$ alkyl, $C_1$–$C_6$ hydroalkyl, $C_1$–$C_6$ alkoxy, ($C_1$–$C_6$)alkoxy($C_1$–$C_4$)alkyl, acryloxy, methacryloxy and halogen, said halogen or (halo) groups being fluoro or chloro, provided that only one of B and B' is said aryl group; and
 (v) B and B' taken together form the saturated bicyclic ring compounds selected from the group consisting of adamantylidene, bornylidene, and norbornylidene.

2. The naphthopyran of claim 1, wherein:
(a) $R_1$ is the group, —C(O)W, W being —$OR_4$ or —N($R_5$)$R_6$, wherein $R_4$ is hydrogen, $C_1$–$C_4$ alkyl, phenyl, mono($C_1$–$C_4$)alkyl substituted phenyl, mono($C_1$–$C_4$)alkoxy substituted phenyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl-($C_1$–$C_2$)alkyl, mono($C_1$–$C_4$)alkoxy substituted phenyl-($C_1$–$C_2$)alkyl, mono($C_1$–$C_4$)alkoxy ($C_2$–$C_3$)alkyl, or $C_1$–$C_4$ haloalkyl, and wherein $R_5$ and $R_6$ are each selected from the group consisting of hydrogen, $C_1$–$C_4$ alkyl, $C_5$–$C_7$ cycloalkyl, phenyl and mono- or di-substituted phenyl, said phenyl substituents being selected from $C_1$–$C_4$ alkyl and $C_1$–$C_4$ alkoxy, said halo substituents being chloro or fluoro;
(b) $R_2$ and each $R_3$ are hydrogen, $C_1$–$C_3$ alkyl, $C_3$–$C_5$ cycloalkyl, substituted or unsubstituted phenyl, or —$OR_7$, wherein $R_7$ is hydrogen, ($C_1$–$C_3$)alkyl, or the group, —CH($R_8$)X, wherein X is CN, or —C(O)W and $R_8$ is hydrogen or methyl, or $R_7$ is the group, C(O)Y, wherein Y is $C_1$–$C_3$ alkyl or $C_1$–$C_3$ alkoxy, and n is selected from the integers 0 and 1;
(c) B and B' are each selected from the group consisting of:
 (i) the groups represented by the following graphic formulae:

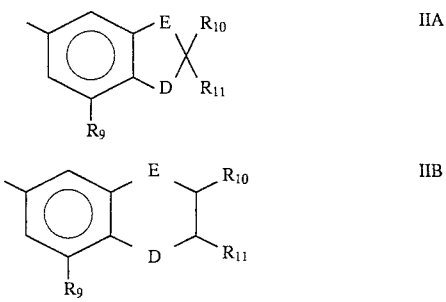

wherein D is oxygen and E is carbon; $R_{10}$ and $R_{11}$ are each hydrogen or $C_1$–$C_3$ alkyl; and $R_9$ is hydrogen;
 (ii) $C_1$–$C_4$ alkyl;
 (iii) substituted or unsubstituted phenyl, and
 (iv) B and B' taken together form the saturated bicyclic ring compound adamantylidene.

3. The naphthopyran of claim 2, wherein:
(a) $R_1$ is the group, —C(O)W, W being the group —$OR_4$, wherein $R_4$ is a $C_1$–$C_3$ alkyl.

4. A photochromic article comprising an organic host material and a photochromic amount of at least one photochromic naphthopyran compound of claim 1.

5. The photochromic article of claim 4 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethane, poly(ethylene terephthalate), polystyrene, copoly(styrene-methylmethacrylate), copoly(styrene-acrylonitrile), polyvinylbutyral and polymers of members selected from the group consisting of polyol(allyl carbonate) monomers, polyfunctional acrylate monomers, and diallylidene pentaerythritol monomers.

6. A photochromic article comprising an organic host material and a photochromic amount of at least one photochromic naphthopyran compound of claim 2.

7. The photochromic article of claim 6 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethane, poly(ethylene terephthalate), polystyrene, copoly(styrene-methylmethacrylate), copoly(styrene-acrylonitrile), polyvinylbutyral and polymers of members selected from the group consisting of polyol(allyl carbonate) monomers, polyfunctional acrylate monomers, and diallylidene pentaerythritol monomers.

8. The photochromic article of claim 7, wherein $R_1$ of the naphthopyran compound is the group —C(O)W, W being the group —OR$_4$, wherein $R_4$ is a $C_1$–$C_3$ alkyl.

9. The photochromic article of claim 8 wherein the organic host material is a solid transparent homopolymer or copolymer of diethylene glycol bis(allyl carbonate), polycarbonate, poly(methylmethacrylate), polyvinylbutyral, or a polyurethane.

10. The photochromic article of claim 9 wherein the photochromic naphthopyran compound is present in an amount of from about 0.15 to 0.35 milligrams per square centimeter of organic host material surface to which the photochromic substance(s) is incorporated or applied.

11. The photochromic article of claim 10 wherein the article is a lens.

12. A photochromic article comprising, in combination, a solid transparent polymerized organic host material and a photochromic amount of:
(a) at least one organic photochromic compound having at least one activated absorption maxima within the visible range of greater than 590 nanometers associated with said host material, and
(b) at least one photochromic naphthopyran compound of claim 1.

13. The photochromic article of claim 12 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethane, poly(ethylene terephthalate), polystyrene, copoly(styrene-methylmethacrylate), copoly(styrene-acrylonitrile), polyvinylbutyral and polymers of members selected from the group consisting of polyol(allyl carbonate) monomers, polyfunctional acrylate monomers, and diallylidene pentaerythritol monomers.

14. A photochromic article comprising, in combination, a solid transparent polymerized organic host material and a photochromic amount of:
(a) at least one organic photochromic compound having at least one activated absorption maxima within the visible range of greater than 590 nanometers associated with said host material, and
(b) at least one photochromic naphthopyran compound of claim 2.

15. The photochromic article of claim 14 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethane, poly(ethylene terephthalate), polystyrene, copoly(styrene-methylmethacrylate), copoly(styrene-acrylonitrile), polyvinylbutyral and polymers of members selected from the group consisting of polyol(allyl carbonate) monomers, polyfunctional acrylate monomers, and diallylidene pentaerythritol monomers.

16. The photochromic article of claim 15 wherein the organic host material is a solid transparent homopolymer or copolymer of diethylene glycol bis(allyl carbonate), polycarbonate, poly(methylmethacrylate), polyvinylbutyral, or a polyurethane.

17. The photochromic article of claim 16 wherein the organic photochromic compound (a) is selected from the group consisting of spiro(indoline)naphthoxazines, spiro(indoline)pyridobenzoxazines, spiro(benzindoline)pyridobenzoxazines, spiro(benzindoline) naphthoxazines, spiro(benzindoline)naphthopyrans, spiro(indoline)benzoxazines, spiro(indoline)benzopyrans, spiro(indoline)naphthopyrans, spiro(indoline)quinopyrans, spiro(indoline)pyrans, 3H-naphtho[2,1-b]pyrans, and mixtures of such photochromic substances.

18. The photochromic article of claim 17 wherein each photochromic compound associated with the organic host material is present in an amount of from about 0.15 to 0.35 milligrams per square centimeter of organic host material surface to which the photochromic compound is incorporated or applied.

19. The photochromic article of claim 18 wherein the article is an ophthalmic lens.

20. A photochromic article comprising, in combination, a solid transparent polymerized organic host material and a photochromic amount of
(a) at least one organic photochromic compound represented by the graphic formula:

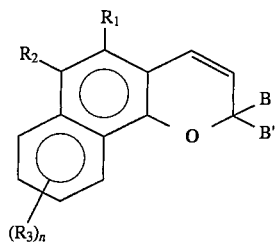

wherein $R_1$ is the group —C(O)W, and wherein W is the group —OR$_4$, $R_4$ being a $C_1$–$C_3$ alkyl; $R_2$ and each $R_3$ are selected from hydrogen, $C_1$–$C_3$ alkyl, or the group —OR$_7$, wherein $R_7$ is hydrogen, $C_1$–$C_3$ alkyl, the group —CH($R_8$)X, wherein X is —C(O)W and $R_8$ is hydrogen or methyl, or $R_7$ is the group —C(O)Y wherein Y is $C_1$–$C_3$ alkyl or $C_1$–$C_3$ alkoxy, and n is the integer 0 or 1; and B and B' are each selected from the group consisting of:
(i) the groups represented by the following graphic formulae:

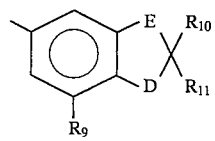
IIA

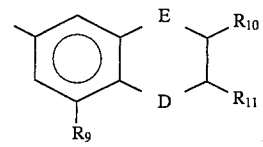
IIB wherein D is oxygen and E is carbon; $R_{10}$ and $R_{11}$ are each hydrogen or $C_1$–$C_3$ alkyl; and $R_9$ is hydrogen;
(ii) $C_1$–$C_4$ alkyl;
(iii) substituted or unsubstituted phenyl, said phenyl substituent being $C_1$–$C_3$ alkyl or $C_1$–$C_3$ alkoxy, and provided that only one of B and B' is said phenyl group, and
(iv) B and B' taken together form the saturated bicyclic ring compound adamantylidene; and
(b) at least one organic photochromic compound selected from the group consisting of spiro(indoline)naphthoxazines, spiro(indoline)pyridobenzoxazines, spiro(indoline)benzoxazines, spiro(indoline)benzopyrans, spiro(indoline)naphthopyrans and 3H-naphtho[2,1-b]pyrans, the weight ratio of the photochromic compounds (a):(b) being from about 1:3 to about 3:1.

21. The photochromic article of claim 20 wherein the organic host material is a solid transparent homopolymer or copolymer of diethylene glycol bis(allyl carbonate), polycarbonate, poly(methylmethacrylate), polyvinylbutyral, or a polyurethane.

22. The photochromic article of claim 21 wherein $R_1$ is the group —C(O)W, W being the group —$OR_4$, $R_4$ being methyl, $R_2$ and each $R_3$ are $C_1$–$C_3$ alkyl or the group —$OR_7$, wherein $R_7$ is $C_1$–$C_3$ alkyl or the group —C(O)Y, wherein Y is $C_1$–$C_3$ alkyl and n is the integer 0 or 1.

23. The photochromic article of claim 22 wherein the organic photochromic compound (b) is selected from spiro(indoline)naphthoxazine or spiro(indoline)pyrido benzoxazines.

24. A naphthopyran compound represented by the following graphic formula:

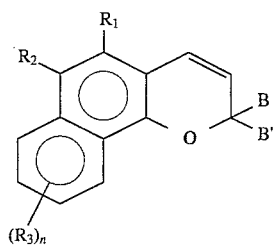

wherein, (a) $R_1$ is the group, —C(O)W, W being —$OR_4$, wherein $R_4$ is a $C_1$–$C_4$ alkyl;

(b) $R_2$ is hydrogen;

(c) $R_3$ is $C_1$–$C_3$ alkyl, and n is the integer 1;

(d) B and B' are each selected from the group consisting of substituted and unsubstituted phenyl, said phenyl substituents being $C_1$–$C_3$ alkyl or $C_1$–$C_3$ alkoxy.

25. The naphthopyran compound of claim 24 wherein B and B' are unsubstituted phenyl.

26. A naphthopyran compound selected from the group consisting of:

(a) 2-(4-Methoxyphenyl)-2-(2-methyl-2,3-dihydrobenzofur-5-yl)-5-methoxycarbonyl-6-(ethoxycarbonyl)methoxy-[2H]-naphtho[1,2-b]pyran;

(b) 2,2-Spiroadamantylene-5-methoxycarbonyl-6-methoxy-[2H]-naphtho[1,2-b]pyran; and (c) 2-(4-methoxyphenyl)-2-t-butyl-5-methoxycarbonyl-6-acetoxy-[2H]-naphtho[1,2-b]pyran.

* * * * *